United States Patent [19]

Gordon

[11] Patent Number: 4,531,936

[45] Date of Patent: Jul. 30, 1985

[54] DEVICE AND METHOD FOR THE SELECTIVE DELIVERY OF DRUGS TO THE MYOCARDIUM

[76] Inventor: Robert T. Gordon, 4936 W. Estes, Skokie, Ill. 60077

[21] Appl. No.: 457,416

[22] Filed: Jan. 12, 1983

Related U.S. Application Data

[63] Continuation-in-part of Ser. No. 229,753, Jan. 29, 1981, abandoned.

[51] Int. Cl.³ ............................................. A61B 19/00
[52] U.S. Cl. ........................................ 604/49; 604/52; 604/53; 604/66; 604/67; 128/1 D
[58] Field of Search .................. 128/1 D, 207.15, 325, 128/344; 604/49, 50, 54, 66, 96, 103, 101, 67, 52, 53

[56] References Cited

U.S. PATENT DOCUMENTS

| | | | |
|---|---|---|---|
| 3,045,677 | 7/1962 | Wallace | 604/101 |
| 3,592,183 | 7/1971 | Watkins | 128/1 R |
| 3,592,184 | 7/1971 | Watkins | 128/1 R |
| 3,692,018 | 9/1972 | Goetz et al. | 128/1 D |
| 4,154,227 | 5/1979 | Krause | 128/1 D |
| 4,301,797 | 11/1981 | Pollack | 128/214 R |

*Primary Examiner*—C. Fred Rosenbaum
*Assistant Examiner*—Mario Costantino
*Attorney, Agent, or Firm*—Lalos, Leeds, Keegan, Marsh, Bentzen & Kaye

[57] ABSTRACT

A device and a method for the selective delivery of drugs or therapeutic agents to the heart. The device consists of a catheter which is introduced into the ascending aorta via the right brachial artery, the femoral artery, or directly. The balloon portion of the catheter is then inflated in the ascending aorta while introducing the drug or therapeutic agent through the distal opening and directly into the coronary arteries. Several doses of the drug or therapeutic agent may be given by delivery in coordination with timed inflation and deflation of the balloon during diastole of the heart. In addition, a two-balloon catheter may be utilized to enhance delivery of the drug or agent to the coronary arteries.

44 Claims, 3 Drawing Figures

A = DISC BALLOON FOR OCCLUDING LUMEN OF AORTA AT APPROPRIATE TIME

B = VOLUME BALLOON FOR HELPING DELIVER DRUG TO THE MYOCARDIUM

DEVICE AND METHOD FOR THE SELECTIVE DELIVERY OF DRUGS TO THE MYOCARDIUM

INTRODUCTION

This application is a continuation-in-part of application Ser. No. 229,753 filed Jan. 29, 1981, now abandoned.

This invention relates to a device and method for the delivery of drugs or therapeutic agents directly to the coronary arteries of the heart and hence to the myocardium.

BACKGROUND OF THE INVENTION

It has long been known that many heart attacks (myocardial infarctions) are caused by clots forming in already partially obstructed coronary arteries secondary to atherosclerotic disease. At this point, time is of the greatest essence in trying to prevent permanent myocardial damage. Accordingly, while attempts have been made to inject substances which will lyse these clots and hopefully avert the myocardial infarction through direct catheterization of the small coronary arteries, their effectiveness has been limited due to the hours often necessary for the procedure together with the extensive equipment required and the intricate catheterization of the coronary arteries involved.

OBJECTS OF THE INVENTION

It is therefore the purpose and principal object of the present invention to deliver drugs and therapeutic agents to the heart directly, simple and quickly.

GENERAL DESCRIPTION OF THE INVENTION

The present invention allows for the introduction of a balloon catheter into the ascending aorta. This catheter may be introduced via the right brachial artery, femoral artery, or directly. It is also within the scope of the present invention to introduce the catheter directly into the ascending aorta via a dacron graft. The catheter is inserted to a level immediately above the aortic valve.

The catheter is approximately 3 mm to 5 mm in diameter with several internal lumens, and the balloon catheter has a volume of 20 cc to 60 cc. One lumen connects a proximal port to a distal open end of the catheter suitable for the injection of drugs or therapeutic agents.

The distal portion of the catheter, approximately 2 cm to 4 cm includes the balloon apparatus. The balloon, which can be disc-like conformation, is connected to an interal lumen which proximally may be connected to any of the devices currently in use for intra-aortic pumping. The balloon volume is 20 cc to 40 cc. The balloon is timed to inflate immediately after left ventricular systole and to deflate just prior to the next ventricular systole. During the period of balloon inflation, the drug or therapeutic agent is injected through the distal opening. Since the aortic valve is competent and the balloon obstructs the distal aortic lumen, the drug or therapeutic agent is forced directly into the coronary arteries during diastole. Diastole incidentially is the best time for filling of the coronary arteries due to the relaxation of the myocardium and of the coronary vessels at this time. This procedure may be repeated many times during many cycles of the heart.

In accordance with the present invention, there are found to be a number of approaches and types of balloon apparatuses that can successfully aid in the direct delivery of drugs or therapeutic agents to the coronary arteries.

In its simplest and broadest aspect, the invention contemplates the use of a single balloon which can be inflated and deflated in the ascending aorta in phase with the left ventricular contractions. The drug or therapeutic agent is injected through the distal opening during diastole and hence directly into the coronary arteries.

A two-balloon system can also be utilized. The first balloon inflates in order to obstruct the aorta during diastole. The drug or therapeutic agent is then delivered via the distal opening and the second balloon is inflated to help drive the drug or therapeutic agent directly into the coronary arteries. This may be repeated at many times during the cardiac cycle, if necessary.

To improve the system, the drug or therapeutic agent may be given through the distal opening under a constant pressure slightly higher than the aortic pressure during diastole. Therefore, the drug or agent will be injected during the diastolic portion of the cardiac cycle but not during the systolic portion of the cardiac cycle when the aortic pressure is higher than the pressure with which the drug is being introduced. Hence the drug is introduced during the proper time of the cardiac cycle and directly into the coronary arteries with the assistance of the inflating and deflating balloon portion of the catheter.

Once damage to the heart begins from a blocked blood vessel, the sooner the blockage is removed, the better is the heart's chance to recover. The present invention introduces the drug or agent to the heart within minutes as opposed to the hours often required with attempts at cardiac catheterization. In addition, the present invention eliminates the requirement for extensive equipment and transportation of the patient to a cardiac catheterization lab, obvious perilous disadvantages experienced in attempts at cardiac catheterization.

DETAILED DESCRIPTION OF THE FIGURES

FIG. 1

Figure 1:
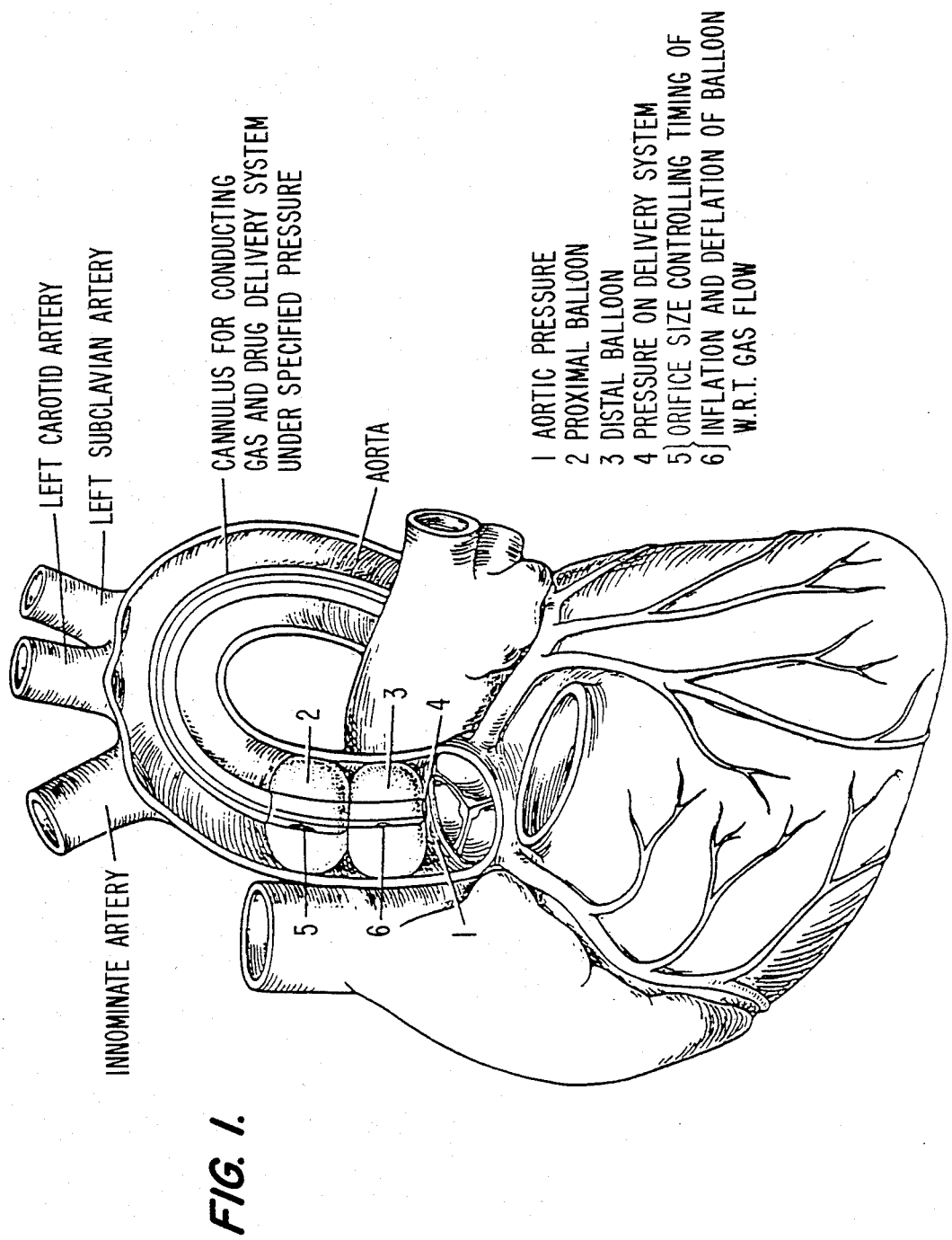
Figure 2:
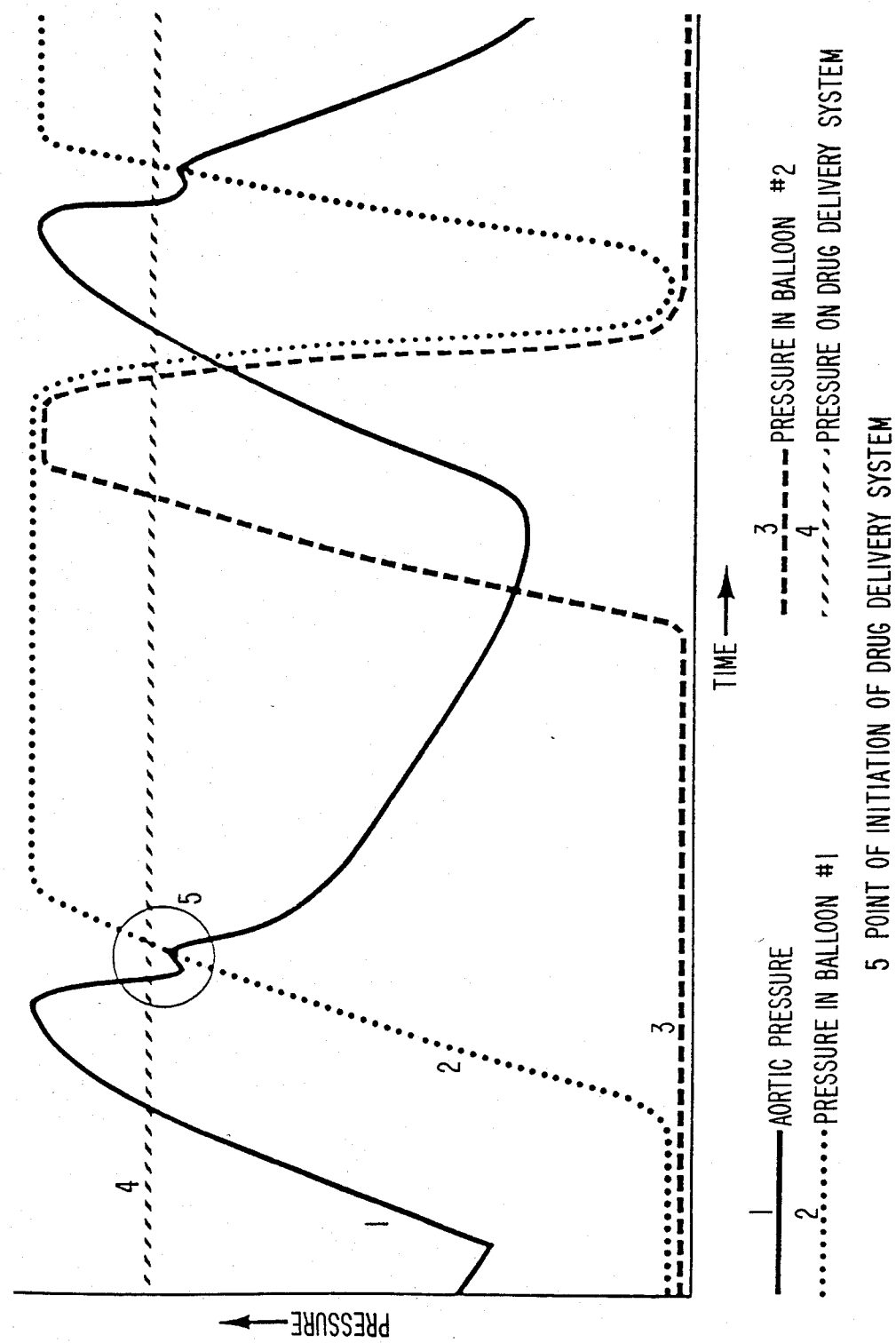

The diagram illustrates the catheter in place immediately adjacent to the openings of the coronary arteries.

(1) The Cannulus for conducting the gas and drug delivery system to the proximal and distal balloon as well as the distal lumen are shown.

The proximal balloon (2) inflates immediately following left ventricular systole as the gas flows through the orifice to the proximal balloon (5).

Once the pressure in the aorta falls below systolic pressure the flow of the drug through the drug delivery system begins through the distal lumen (4).

Since the aortic valve is competennt and the proximal balloon obstructs the distal aortic lumen, the drug or the therapeutic agent is forced directly into the coronary arteries continuously during diastole.

The distal balloon (3) then inflates as gas flows through the orifice (6) to help drive the drug into the coronary arteries. The pressure on the drug delivery system being kept between the systolic and diastolic aortic pressures.

It should be noted that the pressure is monitored by a standard arterial line and while the balloon pressure is not of note, the pressure of the drug being injected is carefully monitored by standard techniques - pressure bags, etc. to keep this pressure above the diastolic pressure but below the systolic pressure of the patient. Also, the method of detection of systole and the proper timing squence are all through currently performed techniques of electrocardiographic monitoring and blood pressure surveillance and are well known to those "skilled in the art." The process which is unique is the continuous injection of a drug during diastole of the heart, directly into the coronary arteries with an increased perfusion obtained by utilizing the two-balloon system.

FIG. 2

The timing sequence for the selective delivery of drugs to the myocardium is shown.

Curve (1) is the aortic pressure as measured through the lumen or via a standard arterial line.

Curve (2) is the pressure in the proximal balloon No. 1 which inflates immediately following systole and deflates immediately prior to the next left ventricular systolic peak.

Curve (3) is the pressure in the distal balloon No. 2 which inflates to drive the drug or therapeutic agent into the coronary arteries and then deflates in sequence with balloon No. 1 immediately prior to the next systolic peak.

Curve (4) represents the pressure on the drug delivery system which is kept below the systolic arterial pressure yet above the diastolic pressure so that drug delivery is continuous during diastole. It is possible to augment this drug delivery pressure once diastole occurs to help drive the drug or therapeutic agent into the coronary arteries.

Point (5) is very important since it represents the point at which the aortic pressure drops below the systolic peak, the aortic valve closes, the proximal balloon No. 1 inflates and the initiation of the drug delivery system begins. Consequently, the drug or therapeutic agent is delivered continuously throughout diastole.

FIG. 3

Figure 3:
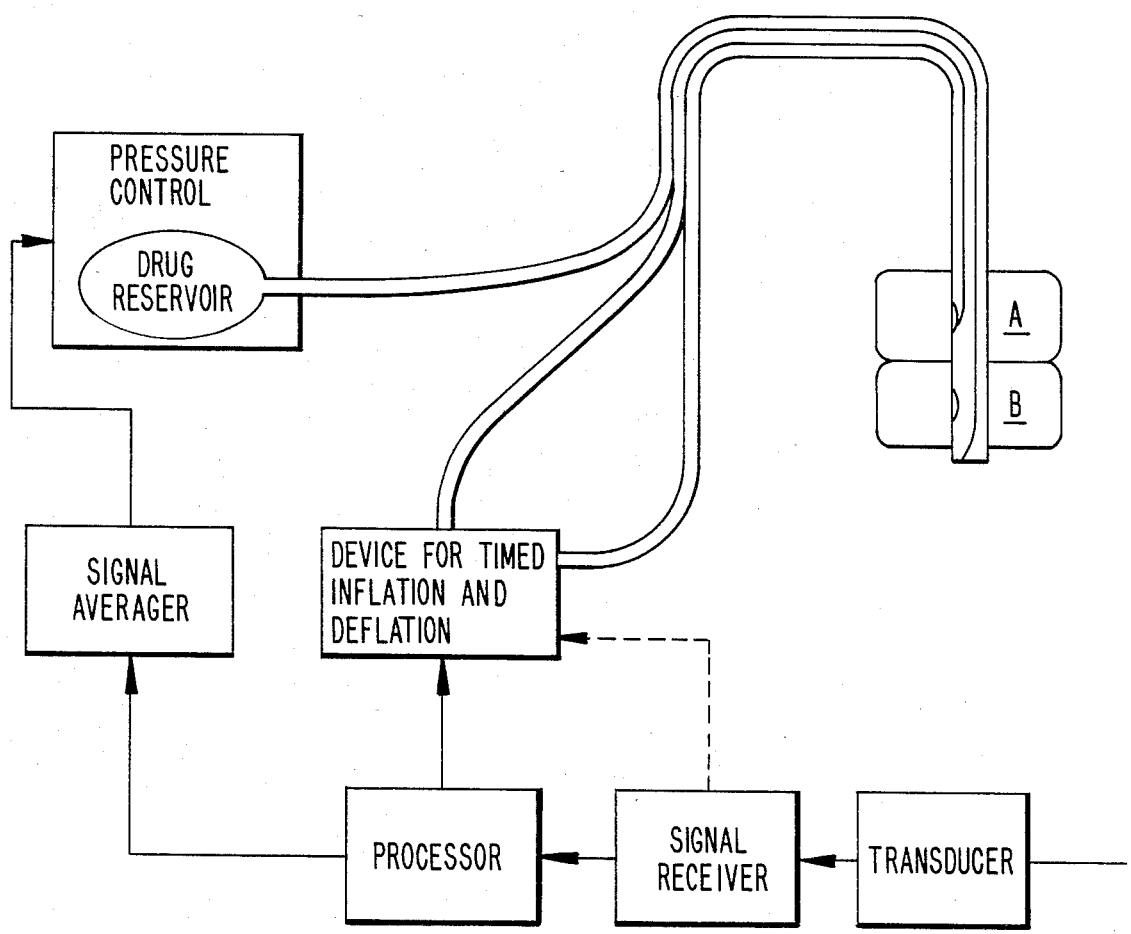

FIG. 3 is a schematic view of a drug delivery system of the present invention.

DETAILED DESCRIPTION OF THE PREFERRED METHODS

Example I

After the subject is placed on the table, the catheter is introduced via a peripheral artery; i.e. the right brachial artery or femoral artery into the ascending aorta. Fluoroscopy is utilized, if necessary. The catheter is positioned immediately above the aortic valve. The lumen connecting to the balloon is then attached to a timing device similar to that used for the intra-aortic balloon. This balloon inflates immediately after systole and the drug or therapeutic agent is injected via the distal opening, and into the coronary arteries. The balloon deflates prior to the next ventricular contraction. The process may be repeated, if necessary. After the procedure is completed the catheter is removed via the peripheral artery.

Example II

The subject is placed on the table and the double-balloon catheter with two-balloons, in series, is introduced via a peripheral artery. The catheter is threaded immediately above the aortic valve. The proximal balloon inflates immediately after systole and the drug or therapeutic agent is injected via the distal opening into the coronary arteries. At this time, the second distal balloon inflates to help drive the agent directly into the coronary arteries. Immediately prior to the next ventricular contraction, both balloons deflate. This process may be repeated through several cardiac cycles, if required. By keeping the pressure on the injected drug or agent slightly higher than the diastolic pressure but lower than the systolic pressure, the drug would only be injected during the diastolic phases of the heart when the coronary arteries can fill the best. At the conclusion of the procedure, the catheter is removed via the peripheral artery.

There are many variations of the invention as described and this invention should be limited solely by the scope of the following claims.

I claim:

1. A process for the selective delivery of drugs or therapeutic agents to the coronary arteries and the heart in a living subject comprising the steps of:
   determining the time of a left ventricular contraction of the subject,
   immediately following said left ventrical contraction, inflating a balloon catheter device, which has a distal opening out through which the drug or therapeutic agent can pass, in the subject's ascending aorta immediately above his aortic valve, to obstruct his aorta,
   after said inflating has started, delivering the drug or therapeutic agent via said balloon catheter device out through said distal opening directly into the subject's coronary arteries continuously and only during diastole by continuously maintaining the drug or therapeutic agent at a pressure greater than the subject's diastolic pressure during diastole and less than the subject's systolic pressure during systole,
   determining the time of the subject's next left ventricular systole following said left ventricular contraction, and
   immediately preceding said next left ventricular systole, deflating said balloon catheter device in the subject's aorta.

2. The process of claim 1 including,
   before said inflating step, introducing said balloon catheter device into the ascending aorta immediately above the subject's aortic valve.

3. The process of claim 2 including,
   said introducing comprising introducing said balloon catheter device into the ascending aorta via a peripheral artery of the subject.

4. The process of claim 2 including,
   said introducing comprising introducing said balloon catheter device directly into the subject's ascending aorta via a dacron graft.

5. The process of claim 1 including,
   repeating said process as necessary.

6. The process of claim 1 including,
   removing said balloon catheter device from the ascending arota via the peripheral artery, after said process is completed.

7. The process of claim 1 including,
   said maintaining step including continuously maintaining, during both systole and diastole, the drug or therapeutic agent at a pressure between the subject's diastolic and systolic pressures.

8. The process of claim 7 including,
   said pressure consisting of a pressure slightly higher than the subject's diastolic pressure.

9. The process of claim 1 including,
   said inflating including temporarily blocking the aortic lumen with the balloon of said balloon catheter device to deliver the drug or therapeutic agent specifically to the myocardium.

10. A process for the selective delivery of drugs or therapeutic agents to the coronary arteries and the heart in a living subject comprising the steps of:

determining the time of a left ventricular contraction of the subject, immediately following said left ventricular contraction, inflating the proximal balloon of a two-balloon catheter device, which has a proximal balloon, a distal balloon, and a distal opening out through which the drug or therapeutic agent can pass, in the subject's ascending aorta immediately above his aortic valve, to obstruct his aorta, after said inflating has started, delivering the drug or therapeutic agent via said balloon catheter device out through said distal opening directly into the subject's coronary arteries continuously and only during diastole by continuously maintaining the drug or therapeutic agent at a pressure greater than the subject's diastolic pressure during diastole and less than the subject's systolic pressure during systole, after said delivering has started, inflating said distal balloon to augment said delivering into the subject's coronary arteries, determining the time of the subject's next left ventricular systole following said left ventricular contraction, and immediately preceding said next left verticular systole, deflating said proximal balloon and said distal balloon in the subject's aorta.

11. The process of claim 10 including,
before said inflating step, introducing said two-balloon catheter device into the subject's ascending aorta immediately above the subject's aortic valve.

12. The process of claim 11 including,
said introducing comprising introducing said two-balloon catheter device directly into the ascending aorta via a peripheral artery.

13. The process of claim 11 including,
said introducing comprising introducing said two-balloon catheter device directly into the ascending aorta via a dacron graft.

14. The process of claim 10 including,
repeating said process as necessary.

15. The process of claim 10 including,
removing said two-balloon catheter device from the ascending aorta via the subject's peripheral artery, after said process is completed.

16. The process of claim 10 including,
said maintaining step including continuously maintaining, during both systole and diastole, the drug or therapeutic agent at a pressure between the subject's diastolic and systolic pressures.

17. The process of claim 10 including,
said pressure consisting of a pressure slightly higher than the subject's diastolic pressure.

18. The process of claim 10 including,
said inflating including temporarily blocking the subject's aortic lumen with said proximal balloon to allow drug delivery specifically to the myocardium.

19. A device for the selective delivery of drugs and therapeutic agents to the coronary arteries and to the heart comprising:
a balloon catheter having a distal opening,
a first determining means operatively connected to said balloon catheter for determining the time of a left ventricular contraction,
an inflating means operatively connected to said balloon catheter for inflating said balloon catheter in the ascending aorta immediately following said left ventricular contraction,
a delivering means operatively connected to said balloon catheter for delivering a drug or an agent via said distal opening of said balloon catheter into the coronary arteries and the heart when said balloon catheter is positioned in the ascending aorta immediately above the aortic valve and after said inflating means has started inflating said balloon catheter,
a second determining means operatively connected to said balloon catheter for determining the time of the next left ventricular systole following said left ventricular contraction whose time was determined by said first determining means, and
a deflating means operatively connected to said balloon catheter for deflating said ballon catheter in the aorta immediately preceding said next left ventricular systole.

20. The device of claim 19 including,
said balloon catheter including at least one internal lumen.

21. The device of claim 20 including,
said balloon catheter including a distal portion connected to said internal lumen and an intra-aortic pumping device to which said internal lumen is proximally connected.

22. The device of claim 19 including,
said balloon catheter including a tip which is open and a proximal port to which said tip is connected for monitoring pressure.

23. The device of claim 19 including,
said balloon catheter comprising a single-balloon catheter.

24. The device of claim 19 including,
said delivering means including an agent delivery system.

25. The device of claim 24 including,
said agent delivery system including liposomes containing the drug.

26. The device of claim 19 including,
said balloon catheter including a balloon which is disc-like in conformation.

27. The device of claim 19 including,
said balloon catheter having a volume of 20 cc to 60 cc.

28. The device of claim 19 including,
said balloon catheter comprising a two-balloon catheter.

29. The device of claim 28 including,
said two-balloon catheter including at least one balloon which is disc-like in conformation.

30. The device of claim 28 including,
said two-balloon catheter including a first proximal balloon and a second distal balloon connected in series with said first proximal balloon.

31. The device of claim 30 including,
said first proximal balloon including a first lumen and said second distal balloon including a second lumen separate from said first lumen and adapted to allow for the separate gas filling of said first proximal balloon and said second distal balloon.

32. The device of claim 30 including, said inflating means inflating said first proximal balloon, said delivering means including a second balloon inflating means for inflating said second balloon, and said deflating means deflating said first proximal balloon and said second distal balloon.

33. The device of claim 32 including, said delivering means including a maintaining means for continuously maintaining the pressure on the drug or agent higher than the diastolic pressure but lower than the systolic pressure.

34. The device of claim 33 including, said injecting means including a giving means for giving the agent through a distal opening of said balloon catheter.

35. The device of claim 30 including, a timing device attached to said internal lumen.

36. The device of claim 19 including, said delivering means being adapted to inject thrombolytic agents.

37. A balloon catheter device for the selective delivery of drugs or therapeutic agents to the coronary arteries and to the heart in a living subject comprising:

a gas-inflatable balloon having a disc shape and a volume of 20 cc to 40 cc, such that when it is positioned in the subject's ascending aorta immediately above his aortic valve and inflated, it obstructs his aorta, a gas conveying-catheter connected to said balloon and having an orifice through which gas can pass into said gas-inflatable balloon to inflate said gas-inflatable balloon and out through which gas can pass to deflate said gas-inflatable balloon, and a drug or therapeutic agent delivering catheter passing through said gas-inflatable balloon when inflated and having one end connectable to a drug or therapeutic agent supply and an opposite end having a distal end opening through which the drug or therapeutic agent is delivered into the subject's coronary arteries and heart during diastole.

38. The device of claim 37 including, said gas-inflatable balloon defining a proximal balloon, and a gas-inflatable distal balloon positioned between said proximal balloon and said distal end and inflatable, after said proximal balloon has inflated and the drugs or therapeutic agents have commenced being delivered out through said distal end opening, to help drive the drug or therapeutic agent directly into the coronary arteries.

39. The device of claim 38 including, said gas conveying catheter passing into said distal balloon and having a distal balloon orifice communicating with the interior of said distal balloon and through which gas can pass into or out of said distal balloon to inflate or deflate said distal balloon.

40. The device of claim 38 including, said orifice of said proximal balloon being larger than said distal balloon orifice such that said distal balloon inflates only after said proximal balloon has inflated.

41. The device of claim 3 including, a cannulus containing said gas-conveying catheter and said drug or therapeutic agent delivering catheter.

42. The device of claim 41 including, said cannulus being 3 mm to 5 mm in diameter.

43. The device of claim 38 including, said proximal balloon including a first lumen and said distal balloon including a second lumen separate from said first lumen and adapted to allow for the separate gas filling of said first proximal balloon and said second distal balloon.

44. The deviced of claim 37 including, said drug or therapeutic agent delivering catheter including an open distal end tip and a proximal port to which said open distal end tip is connected for monitoring pressure of the drug or therapeutic agent.

* * * * *